(12) United States Patent
Chen et al.

(10) Patent No.: US 8,900,717 B2
(45) Date of Patent: Dec. 2, 2014

(54) METHODS FOR PRODUCING SYNTHETIC SURFACES THAT MIMIC COLLAGEN COATED SURFACES FOR CELL CULTURE

(75) Inventors: Xiaoxi (Kevin) Chen, Westborough, MA (US); Kristina Parry, Rotherham (GB); Anita Mistry, Sheffield (GB); Deepa Saxena, Framingham, MA (US)

(73) Assignee: Corning Incorporated, Corning, NY (US)

( * ) Notice: Subject to any disclaimer, the term of this patent is extended or adjusted under 35 U.S.C. 154(b) by 270 days.

(21) Appl. No.: 13/471,608

(22) Filed: May 15, 2012

(65) Prior Publication Data

US 2012/0225485 A1 Sep. 6, 2012

Related U.S. Application Data

(62) Division of application No. 12/766,961, filed on Apr. 26, 2010, now Pat. No. 8,197,910.

(60) Provisional application No. 61/172,909, filed on Apr. 27, 2009.

(51) Int. Cl.
| | |
|---|---|
| *B32B 9/02* | (2006.01) |
| *B32B 9/04* | (2006.01) |
| *C12N 5/00* | (2006.01) |
| *B05D 1/00* | (2006.01) |

(52) U.S. Cl.
CPC .............. *C12N 5/0068* (2013.01); *B05D 1/62* (2013.01); *C12N 2533/20* (2013.01); *C12N 2533/30* (2013.01); *Y10S 428/936* (2013.01); *Y10S 428/938* (2013.01)
USPC ............................ 428/473; 428/936; 428/938

(58) Field of Classification Search
CPC ........................................................ C12N 5/00
USPC .......................................... 428/473, 936, 938
See application file for complete search history.

(56) References Cited

U.S. PATENT DOCUMENTS 5,876,753 A 3/1999 Timmons et al.

FOREIGN PATENT DOCUMENTS

| EP | 0092302 A2 | 10/1983 |
|---|---|---|
| WO | 2006/010278 A1 | 2/2006 |

OTHER PUBLICATIONS

Koo, Lily Y. et al., "Co-regulation of cell adhesion by nanoscale RGD organization and mechanical stimulus", Journal of Cell Science, Cambridge University Press, London, GB, vol. 115, No. 7, Apr. 1, 2002, pp. 1423-1433.

Martins, Albino et al., "Surface Modification of Electrospun Polycaprolactone Nanofiber Meshes by Plasma Treatment to Enhance Biological Performance", Small, Feb. 25, 2009, vol. 5, No. 10, pp. 1195-1206.

Steele, John G., "Adsorption of fibronectin and vitronectin onto Primaria TM and tissue culture polystyrene and relationship to the mechanism of initial attachment of human vein endothelial cells and BHK-21 fibroblasts", Biomaterials, Jan. 1, 1995, vol. 16, No. 14, pp. 1057-1067.

*Primary Examiner* — Duc Truong
(74) *Attorney, Agent, or Firm* — Hoffmann & Baron, LLP

(57) ABSTRACT

The present invention discloses methods for producing synthetic surfaces that mimic collagen coated surfaces for cell culture comprising: providing a monomer source comprising one or more organic compounds which are capable of polymerization, wherein at least one organic compound is prolinol; creating a plasma of said monomer source; and contacting at least a portion of a surface with the plasma to provide a plasma polymer coated surface. Advantageously, such methods provide an animal-free, synthetic, chemically defined surface that mimics a collagen coated surface for cell culture. Advantageously, such methods not only reduce the cost and/or issues associated with animal-derived collagen but are also amenable to large scale manufacturing.

7 Claims, 1 Drawing Sheet

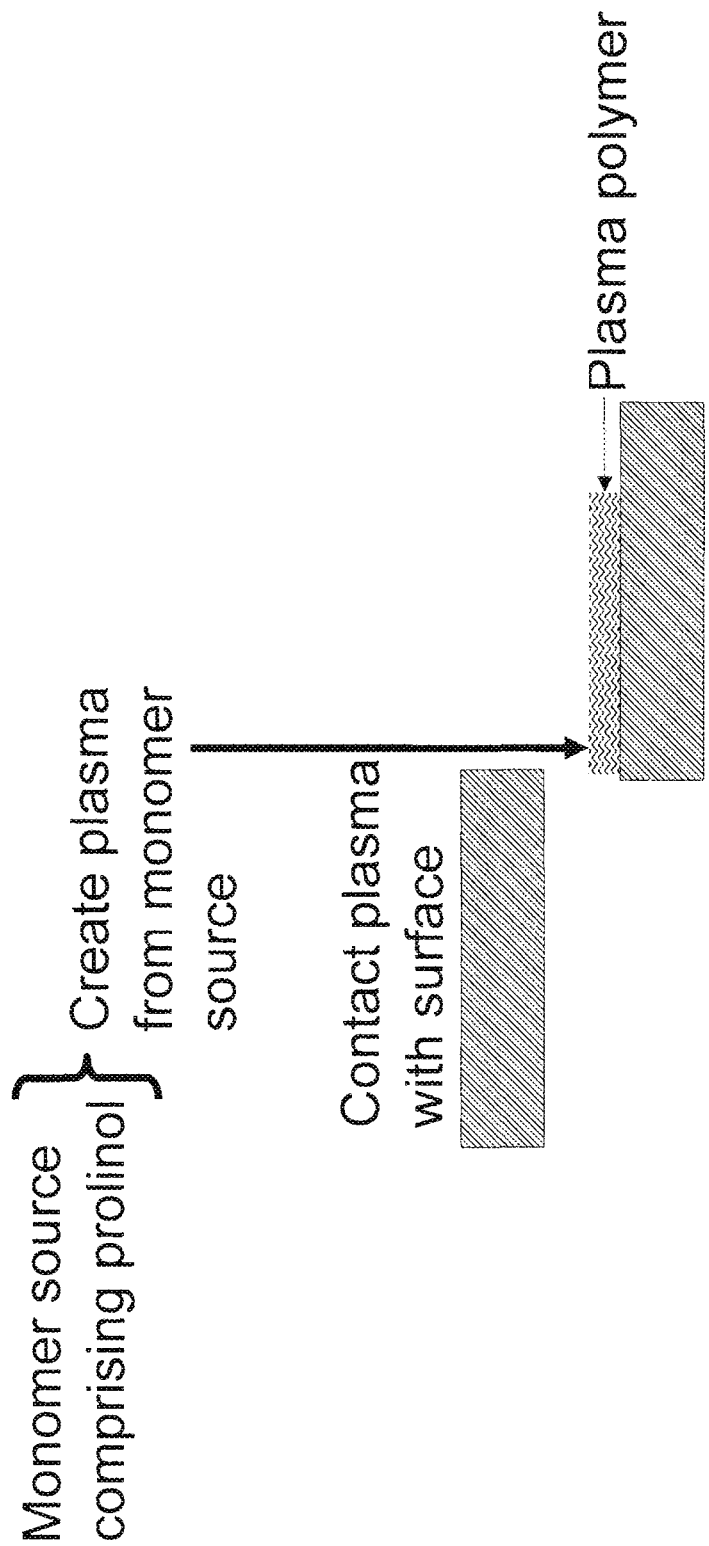

US 8,900,717 B2

METHODS FOR PRODUCING SYNTHETIC SURFACES THAT MIMIC COLLAGEN COATED SURFACES FOR CELL CULTURE

CROSS-REFERENCES TO RELATED APPLICATIONS

This application is a division of U.S. application Ser. No. 12/766,961, filed Apr. 26, 2010, now U.S. Pat. No. 8,197,910, which claims priority to U.S. Provisional Patent Application No. 61/172,909, filed Apr. 27, 2009, the entire contents of these disclosures being incorporated by reference.

FIELD OF THE INVENTION

The present invention relates to methods for producing synthetic surfaces that mimic collagen coated surfaces as well as surfaces prepared by such methods.

BACKGROUND OF THE INVENTION

Collagen coated surfaces have been widely used in cell culture to promote attachment of fastidious cells, including primary cells such as hepatocytes and keratinocytes. Generally, collagen derived from a non-human animal (e.g., rat tail) is employed to coat surfaces for cell culture. However, the use of such collagen can be problematic, for example, in human therapeutic applications. Although human collagen can be used for coating such surfaces, the cost is very high. Likewise, although surfaces coated with peptide sequences that mimic collagen coated surfaces have also been made to culture cells, the cost of producing such surfaces is relatively high and simply not suitable for large scale manufacturing. Thus, there is a need for methods to produce animal-free, synthetic, chemically defined surfaces that mimic collagen coated surfaces which are less costly than those presently available and suitable for large scale manufacturing as well as surfaces produced by such methods.

SUMMARY OF THE INVENTION

The present invention discloses methods for producing animal-free, synthetic, chemically defined surfaces that mimic collagen coated surfaces for cell culture. Advantageously, such methods not only reduce the cost and/or issues associated with animal-derived collagen but are also amenable to large scale manufacturing.

In particular, the present invention provides methods for producing a synthetic surface that mimics a collagen coated surface for cell culture comprising:
i) providing a monomer source comprising one or more organic compounds which are capable of polymerization, wherein at least one organic compound is prolinol;
ii) creating a plasma of the monomer source; and
iii) contacting at least a portion of a surface with the plasma to provide a plasma polymer coated surface wherein the plasma polymer coated surface mimics one or more functional characteristics of a collagen coated surface.
In addition, the present invention provides surfaces useful for cell culture produced by the methods described above.

The present invention also provides a surface for cell culture wherein at least a portion of the surface comprises a coating of prolinol.

The present invention further provides a surface for cell culture wherein at least a portion of the surface comprises a coating comprising a single type of amino acid wherein the single type of amino acid is proline.

These and other features of the invention will be better understood through a study of the following detailed description.

BRIEF DESCRIPTION OF THE FIGURE

FIG. 1 is a flowchart representing a method in accordance with the subject invention.

DETAILED DESCRIPTION OF THE INVENTION

The present invention discloses methods for producing a synthetic surface that mimics a collagen coated surface for cell culture. Likewise, the present invention provides surfaces useful for cell culture. Collagen is a triple helical coiled coil structure with a regular arrangement of amino acids in each of the helical unit. The sequence often follows the pattern Gly-Pro-Y or Gly-X-Hyp (hydroxyproline), where X and Y may be any of various amino acid residues and wherein the motif Gly-Pro-Hyp occurs frequently.

Though not meant to be limited by any theory with the subject invention, a proline-like monomer fixed or immobilized to a surface may mimic one or more functional characteristics of a collagen coated surface. Preferably, the proline-like monomer is fixed by plasma polymerization. Generally, monomers with relatively high vapor pressure are required so that a monomer can readily be introduced into the vacuum chamber as a vapor during the polymerization process. For example, monomers commonly used in plasma polymerization, such as allylamine and acrylic acid, have relatively high vapor pressure. In contrast, monomers with relatively low vapor pressure, such as amino acids, although useable, are not preferred for use in plasma polymerization.

Prolinol, a commercially available chiral amino-alcohol (e.g., D-Prolinol is available from Sigma-Aldrich under Catalog No. 81744) is a derivative of proline. As prolinol is a liquid with greater vapor pressure than the amino acid proline, prolinol is more amenable for use as a monomer source in creating a plasma for coating a surface therewith. In particular, treating a surface for cell culture by plasma polymerization of prolinol provides a synthetic surface that mimics a collagen coated surface. In fact, human hepatocytes are able to attach to a surface coated with prolinol alone without any further extracellular matrix protein coating.

For plasma polymerization, the cell culture vessels to be coated are loaded into a chamber of a plasma polymerization reactor. The chamber is then pumped down to create a vacuum. The vapor of monomer source comprising prolinol is introduced into the chamber. A radio-frequency power is then turned on to initiate the polymerization of prolinol on the surface(s) of the cell culture vessels inside the chamber.

In one embodiment, a RF excited plasma is employed for plasma polymerization. However, any method of generating a gaseous plasma may be used, for example a glow discharge or a corona discharge. For example, microwave frequencies may be employed instead of, or in addition to, RF excitation.

In one embodiment, the plasma is a pulsed plasma. Exemplary conditions for plasma polymerization wherein the plasma is pulsed include, but are not limited to, an on/off pulse of 1 ms/50 ms and an RF power of 100 W; an on/off pulse of 10 ms/100 ms and an RF power of 5 W; on/off pulse of 30 ms/100 ms and an RF power of 5 W; and on/off pulse of 5 ms/50 ms and an RF power of 100 W.

In another embodiment, the plasma is a continuous wave plasma. Exemplary conditions for plasma polymerization wherein the plasma is a continuous wave plasma include, but are not limited to, an RF power of 5 W.

Gases typically used with plasma treatment and introduced into the plasma chamber include Ar, He, Ne, He, He/$H_2$, $O_2$, $N_2$, $NH_3$, and $CF_4$.

In one embodiment, prolinol is deposited onto the surface by plasma polymerization. A flowchart depicting a method for producing a synthetic surface by plasma polymerization of prolinol is shown in FIG. 1. In one embodiment, the surface mimics one or more functional characteristics of a collagen coated surface. In one embodiment, human hepatocytes attach to the coating. In one embodiment, the coating consists essentially of prolinol.

Alternative means for coating a surface with prolinol include, but are not limited to, chemical vapor deposition or immobilization by covalent attachment to one or more carboxyl functional groups, one or more amine functional groups or a combination thereof. Notably, chemical vapor deposition is discussed in Dobkin and Zuraw (Dobkin and Zuraw (2003). Principles of Chemical Vapor Deposition. Kluwer). In one embodiment, prolinol is deposited onto the surface by chemical vapor deposition.

In another embodiment, prolinol is immobilized on the surface by covalent attachment to one or more carboxyl functional groups, one or more amine functional groups or a combination thereof. It is understood that for covalent attachment, the surface may require pre-activation such that the surface comprises one or more carboxyl functional groups, one or more amine functional groups or a combination thereof to facilitate the binding of prolinol thereto. Exemplary means of covalent immobilization of prolinol include, but are not limited to, providing a carboxyl functionalized surface (i.e., wherein the carboxyl groups are activated) using carbodiimide chemistry (e.g., EDC/NHS) followed by linking of prolinol to such surface through an amine reaction with the NHS groups on the surface. Alternatively, covalent immobilization may be achieved by providing an aldehyde functionalized surface followed by linking prolinol to such surface through an amine reaction with the aldehyde groups on the surface through Schiff base formation followed by stabilization of the Schiff base through sodium borohydride reduction.

Similarly, though not meant to be limited by theory with the subject invention, a single type of amino acid, e.g., proline, fixed or immobilized to a surface may mimic one or more functional characteristics of a collagen coated surface. Notably, proline makes up about 9% of collagen.

In one embodiment, proline is immobilized by covalent attachment to one or more carboxyl functional groups, one or more amine functional groups or a combination of two or more thereof. In one embodiment, the surface mimics one or more functional characteristics of a collagen coated surface. In one embodiment, human hepatocytes attach to the coating. In one embodiment, the coating consists essentially of proline.

Exemplary means for coating a surface with proline include, but are not limited to, covalent attachment to one or more carboxyl functional groups, one or more amine functional groups or a combination thereof. It is understood that for covalent attachment, the surface may require pre-activation such that the surface comprises one or more carboxyl functional groups, one or more amine functional groups or a combination thereof to facilitate the binding of proline thereto.

Similar to covalent immobilization of prolinol, exemplary means of covalent immobilization of proline include, but are not limited to, providing a carboxyl functionalized surface (i.e., wherein the carboxyl groups are activated) using carbodiimide chemistry (e.g., EDC/NHS) followed by linking of proline to such surface through an amine reaction with the NHS groups on the surface. Alternatively, covalent immobilization may be achieved by providing an aldehyde functionalized surface followed by linking proline to such surface through an amine reaction with the aldehyde groups on the surface through Schiff base formation followed by stabilization of the Schiff base through sodium borohydride reduction.

In one embodiment, the surface is a multiwell plate, a dish, or a flask. In one embodiment, the monomer source consists essentially of prolinol.

The phrase "mimics one or more functional characteristics of a collagen coated surface" as used herein with reference to a surface coated with prolinol or proline includes but is not limited to functional characteristics of collagen that includes attachment of cells to a collagen coated surface. For example, the attachment of human hepatocytes to a collagen coated surface. In one embodiment, one or more functional characteristics of a collagen coated surface comprises attachment by human hepatocytes.

EXAMPLE A

To explore the ability of the prolinol-coated surface to mimic one or more functional characteristics of a collagen coated surface, human hepatocytes were seeded and monitored on both collagen-coated and prolinol-coated surfaces under the same culture conditions. In brief, cryopreserved hepatocytes were removed from liquid nitrogen storage and immediately placed in a 37° C. waterbath until the cells were nearly thawed. The contents were then transferred to 50 mls of pre-warmed ISOM's Seeding Media. The tubes were centrifuged in a Low-speed centrifuge at 50×g for 5 minutes at room temperature. The supernatant fluid was aspirated and discarded. The cell pellet was resuspended in 1-2 mLs of ISOM's Seeding Media. Cells were counted and then diluted to a density of $10^6$ cells/ml ISOM's Seeding Media. Cells were seeded at a density of $4 \times 10^5$ cells/well (i.e., a volume of 400 mL/well of $10^6$ cells/mL) onto a 24-well plate. Specifically, a prolinol coated or Collagen Type I coated plate. The plates were placed in an incubator at 37° C. with 5% $CO_2$ for about 4 hrs. After such time, the ISOM's Seeding Media was aspirated and cells were fed with 400 µL/well of HepatoSTIM™ media (BD, Catalog #355056). Hepatocyte cell attachment was observed after 24 hours.

In addition, cell attachment and spreading on the surfaces were analyzed and microscopic images taken following several days of cell culture. Notably, human hepatocyte attachment to the prolinol-coated surface is similar to that observed for a collagen-coated surface. Moreover, it should be noted that human hepatocytes attached to the prolinol-coated surface without any further extracellular matrix protein coating.

What is claimed is:

1. A surface for cell culture wherein at least a portion of the surface comprises a coating of prolinol.

2. The surface of claim 1, wherein prolinol is deposited onto the surface by plasma polymerization.

3. The surface of claim 1, wherein prolinol is deposited onto the surface by chemical vapor deposition.

4. The surface of claim 1, wherein prolinol is immobilized on the surface by covalent attachment to one or more carboxyl functional groups, one or more amine functional groups or a combination thereof.

5. The surface of claim 1, wherein the surface mimics one or more functional characteristics of a collagen coated surface.

6. The surface of claim 1, wherein human hepatocytes attach to the coating.

7. The surface of claim 1, wherein the coating consists essentially of prolinol.

* * * * *